United States Patent
Gunderson et al.

(10) Patent No.: US 8,521,269 B1
(45) Date of Patent: Aug. 27, 2013

(54) DETERMINING TACHYARRHYTHMIA DETECTION PARAMETERS BASED ON PRIOR DETECTED EPISODES

(75) Inventors: Bruce D. Gunderson, Plymouth, MN (US); Amisha S. Patel, Troy, MI (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/534,124

(22) Filed: Jun. 27, 2012

(51) Int. Cl.
*A61B 5/0464* (2006.01)

(52) U.S. Cl.
USPC .......................................................... 600/518

(58) Field of Classification Search
USPC .......................................................... 600/518
See application file for complete search history.

(56) References Cited

U.S. PATENT DOCUMENTS

| | | | |
|---|---|---|---|
| 4,374,382 A | 2/1983 | Markowitz | |
| 5,117,824 A | 6/1992 | Keimel | |
| 5,545,186 A | 8/1996 | Olson | |
| 5,755,736 A | 5/1998 | Gillberg | |
| 5,855,593 A | 1/1999 | Olson | |
| 6,052,620 A | 4/2000 | Gillberg | |
| 6,216,036 B1 * | 4/2001 | Jenkins et al. | 607/27 |
| 6,249,701 B1 | 6/2001 | Rajasekhar | |
| 6,418,346 B1 | 7/2002 | Nelson | |
| 6,442,433 B1 | 8/2002 | Linberg | |
| 6,449,503 B1 | 9/2002 | Hsu | |
| 6,480,745 B2 | 11/2002 | Nelson | |
| 6,567,691 B1 | 5/2003 | Stadler | |
| 6,599,250 B2 | 7/2003 | Webb | |
| 6,708,058 B2 | 3/2004 | Kim | |
| 7,031,771 B2 | 4/2006 | Brown | |
| 7,149,577 B2 | 12/2006 | Sharma | |
| 7,317,942 B2 | 1/2008 | Brown | |
| 7,783,354 B2 | 8/2010 | Gunderson | |
| 7,792,578 B2 | 9/2010 | Belk | |
| 7,894,893 B2 | 2/2011 | Kim | |
| 7,930,024 B2 | 4/2011 | Ousdigian | |
| 7,933,651 B2 | 4/2011 | Cazares | |
| 8,073,536 B2 | 12/2011 | Gunderson | |
| 8,073,537 B2 | 12/2011 | Gunderson | |
| 8,249,707 B2 | 8/2012 | Nabutovsky | |
| 2003/0191403 A1 | 10/2003 | Zhou | |
| 2006/0025824 A1 | 2/2006 | Freeman | |
| 2007/0135864 A1 * | 6/2007 | Gunderson et al. | 607/59 |
| 2009/0131999 A1 | 5/2009 | Li | |
| 2009/0259269 A1 | 10/2009 | Brown | |
| 2010/0198290 A1 | 8/2010 | Jackson | |
| 2011/0111525 A1 | 5/2011 | Struck | |
| 2011/0112597 A1 * | 5/2011 | Snell et al. | 607/27 |
| 2011/0251504 A1 | 10/2011 | Tereshchenko | |

\* cited by examiner

*Primary Examiner* — Christopher D Koharski
*Assistant Examiner* — Michael Carey
(74) *Attorney, Agent, or Firm* — Michael C. Soldner

(57) ABSTRACT

A system including a communication module, a processor and a medical device configured to sense cardiac signals and detect cardiac rhythm episodes is configured to retrieve stored episode data accumulated by the medical device and generate truthed episode classifications from the retrieved episode data. The processor is configured to perform a detection simulation for detecting and classifying cardiac rhythm episodes included in the retrieved episode data to obtain simulated episode classifications. Sensitivity and specificity data is generated in response to the detection simulation, and recommended detection parameter settings are identified in response to the sensitivity and specificity data.

25 Claims, 7 Drawing Sheets

DETERMINING TACHYARRHYTHMIA DETECTION PARAMETERS BASED ON PRIOR DETECTED EPISODES

FIELD OF THE DISCLOSURE

The disclosure relates generally to medical devices and, in particular, to a system and method for selecting tachyarrhythmia detection parameters used by a medical device.

BACKGROUND

Implantable medical devices (IMDs), including pacemakers and cardioverter-defibrillators (ICDs), record cardiac electrogram (EGM) signals for detecting the heart rhythm and responding as needed with pacing therapy or high-voltage cardioversion/defibrillation therapy. Numerous criteria may be applied to the EGM signals for detecting arrhythmia episodes and for discriminating between different types of arrhythmias, such as supraventricular tachycardia (SVT), ventricular tachycardia (VT) and ventricular fibrillation (VF). Forms of SVT, including sinus tachycardia, atrial fibrillation or atrial flutter, can be referred to as "non-treatable" or "non-shockable" rhythms in that typically a cardioversion/defibrillation shock delivered to the heart is undesirable for treating these more benign rhythms. Sustained VT and VF, on the other hand, can be referred to as "treatable" or "shockable" rhythms because such sustained rhythms are more serious and potentially life-threatening. Detection of a sustained VT or VF is generally treated by anti-tachycardia pacing (ATP) or a cardioversion/defibrillation shock. One important goal of a tachyarrhythmia detection algorithm is to detect all treatable VT and VF episodes.

SVT is sometimes inappropriately detected as VT or VF, which can result in the patient receiving an unnecessary cardioversion/defibrillation shock. Reducing the likelihood of inappropriate detections of SVT as VT or VF to reduce inappropriate shocks is another goal in designing detection algorithms and setting detection parameters used by the IMD.

Currently, clinicians may modify detection parameters used by the IMD if any inappropriate cardioversion or defibrillation therapies are delivered. However the process of manually reviewing arrhythmia episodes recorded by the IMD and modifying detection parameters is highly time-consuming and requires considerable technical expertise. Selecting which detection parameters to modify and exactly how to modify them can be challenging. As such, a need remains for a system and method that provides a determination of recommended tachyarrhythmia detection parameters for a given patient without placing undue burden on the clinician and that reduces the likelihood of future inappropriate detections and shock delivery.

DETAILED DESCRIPTION

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Figure 1:
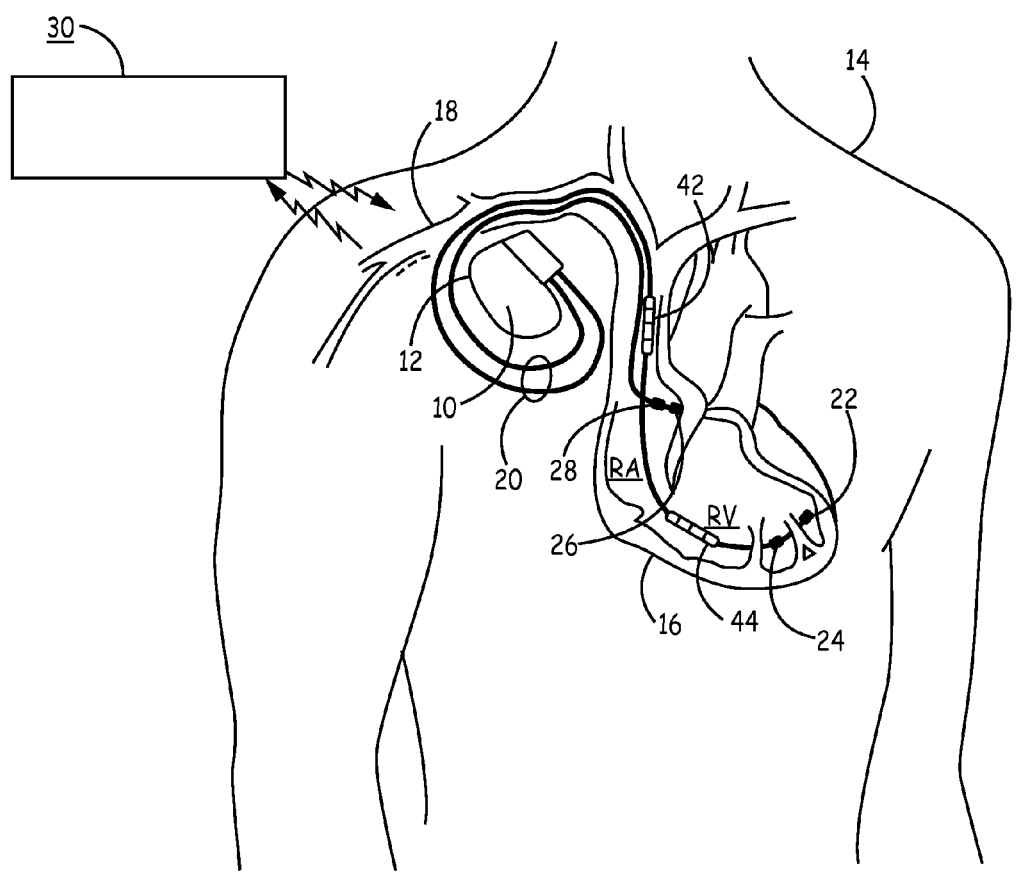
FIG. 1 is a schematic diagram of an implantable medical device system according to one embodiment.

FIG. 1 is a schematic diagram of an implantable medical device system 8 according to one embodiment. As illustrated in FIG. 1, a system 8 for sensing cardiac events (e.g. P-waves and R-waves) and detecting and discriminating tachyarrhythmia episodes includes IMD 10, such as an ICD capable of delivering pacing, cardioversion and defibrillation therapy to the heart 16 of a patient 14.

One or more leads, collectively identified with reference numeral 20 in FIG. 1, are electrically coupled to the IMD 10 and extend into the patient's heart 16 via a vein 18. Leads 20 include electrodes 22 and 24 shown positioned in the patient's right ventricle (RV) and electrodes 26 and 28 positioned in the patient's right atrium (RA) for sensing EGM signals and pacing in the RV and RA, respectively. When IMD 10 is embodied as an ICD, leads 20 additionally carry high voltage coil electrodes 42 and 44 used to deliver cardioversion and defibrillation shock pulses. The leads 20 are used to acquire intracardiac EGM signals from the patient 14 and to deliver therapy in response to the acquired data. In some embodiments, system 8 may include a coronary sinus lead extending into the right atrium, through the coronary sinus and into a cardiac vein to position electrodes along the left ventricle (LV) for sensing LV EGM signals and pacing the LV.

IMD circuitry and associated battery(ies) are housed within a sealed housing 12, which may itself be conductive so as to serve as an electrode for use as an indifferent electrode during pacing or sensing or as an active electrode during defibrillation. As such, housing 12 is also referred to herein as "housing electrode" 12.

The IMD 10 may be implemented as other medical devices, such as a pacemaker, a drug delivery system, a cardiac monitor, a neurostimulator or any other device which includes sensing capabilities and electrodes for acquiring signals of cardiac electrical events. The embodiments described herein relate primarily to an ICD acquiring cardiac EGM signals, detecting cardiac rhythm episodes such as SVT, VT and VF in response to the sensed cardiac event signals, and delivering therapies in response to detected episodes according to programmed therapy menus. The techniques disclosed herein, however, may be implemented in any implantable or external device used to acquire cardiac electrical signals and detect cardiac rhythm episodes of tachycardia or fibrillation.

The EGM signal data acquired by IMD 10 can be transmitted to an external device 30, which may be embodied as a programmer, e.g. used in a clinic or hospital to communicate with IMD 10 via wireless telemetry. External device 30 may alternatively be embodied as a computer, home monitor, or hand-held device including cell phones, smart phones or the like, enabled to communicate directly or indirectly with IMD 10 for retrieving EGM signal data acquired by IMD 10. External device 30 may be coupled to a remote patient monitoring system, such as Carelink®, available from Medtronic, Inc., Minneapolis, Minn. IMD 10 is configured to sense cardiac signals and detect cardiac rhythm episodes from the sensed cardiac signals in real time using a detection algorithm implemented in IMD 10 and controlled by programmable rhythm detection parameters. External device 30 is used to retrieve cardiac rhythm episode data accumulated and stored by IMD 10 for use in identifying recommended settings for the detection parameters and for programming the recommended settings in IMD 10.

Figure 2:
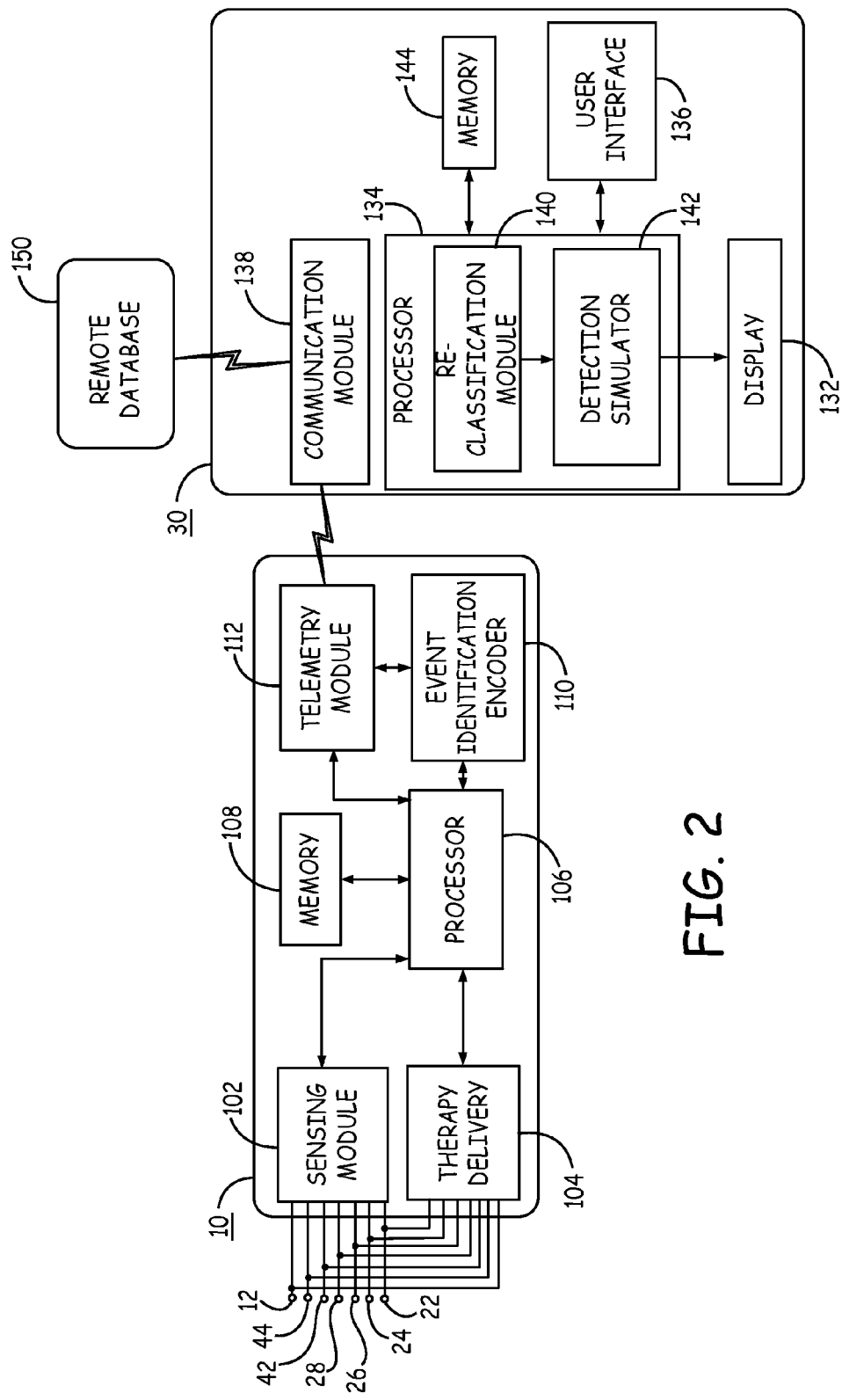
FIG. 2 is a functional block diagram of the system shown in FIG. 1 according to one embodiment.

FIG. 2 is a functional block diagram of system 8 according to one embodiment. System 8 is provided for performing post-processing of cardiac rhythm episode data for identifying recommended cardiac rhythm detection and classification parameters for a given patient for reaching a targeted detection sensitivity and specificity. System 8 retrieves cardiac episode data accumulated by IMD 10 from the patient, reclassifies episodes as necessary using a post-processing reclassification algorithm and/or manual expert "truthing" of reclassified episodes, and executes a detection simulation of retrieved cardiac rhythm episodes for identifying recommended parameters considered to be optimal for detecting and classifying a cardiac rhythm based on sensitivity and specificity targets.

The detection simulation is performed by system 8 using the same detection algorithm implemented in IMD 10. The detection simulation is performed on the retrieved cardiac rhythm episode data using varied settings of the detection parameters to obtain simulated episode classifications made using the varied detection parameter settings. A comparison of the detection simulation classifications with the truthed episode classifications yields sensitivity and specificity data. Recommended detection parameter settings are identified in response to the sensitivity and specificity data.

System 8 includes the IMD 10, external device 30, referred to hereafter as "programmer" 30 though alternatively embodied as a home monitor, handheld or other device configured to communicate with IMD 10. System 8 may additionally include a remote database 150 in communication with programmer 30 and IMD 10. The post-processing techniques described herein may be performed by a processor 106 included in IMD 10, processor 134 included in programmer 30, or a processor associated with remote database 150 after accumulating cardiac rhythm episode data recorded from a given patient in memory accessible by the processing device. The processing functions described may be implemented in IMD 10, programmer 30, or remote database 150 or any combination thereof in a distributed manner.

IMD 10 includes a sensing module 102, a therapy delivery module 104, a processor 106 and associated memory 108, an event identification encoder 110, and a telemetry module 112. Memory 108 may include computer-readable instructions that, when executed by processor 106, cause IMD 10 and processor 106 to perform various functions attributed throughout this disclosure to IMD 10 and processor 106. The computer-readable instructions may be encoded within memory 108. Memory 108 may comprise computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

Processor 106 and other processor units described herein may include any one or more of a microprocessor, a controller, a digital signal processor (DSP), an application specific integrated circuit (ASIC), a field-programmable gate array (FPGA), or equivalent discrete or integrated logic circuitry. In some examples, processor 106 may include multiple components, such as any combination of one or more microprocessors, one or more controllers, one or more DSPs, one or more ASICs, or one or more FPGAs, as well as other discrete or integrated logic circuitry. The functions attributed to processors described herein may be embodied as software, firmware, hardware or any combination thereof. In one example, event identification encoder 110 may, at least in part, be stored or encoded as instructions in memory 108 that are executed by processor 106.

Processor 106 includes a therapy control unit that controls therapy delivery module 104 to deliver electrical stimulation therapy, e.g., cardiac pacing, anti-tachyarrhythmia therapy, or shock pulses, to heart 16 according to a selected one or more therapy programs, which may be stored in memory 108. Therapy delivery module 104 is electrically coupled to electrodes 22, 24, 26, 28, 42, 44 and housing electrode 12 (all of which are shown in FIG. 1). Therapy delivery module 104 is configured to generate and deliver electrical stimulation therapy to heart 16 via selected combinations of electrodes 22, 24, 26, 28, 42, 44, and housing electrode 12.

Sensing module 102 monitors cardiac electrical signals for sensing cardiac electrical signals attendant to the depolarization of myocardial tissue, e.g. P-waves and R-waves, from selected ones of electrodes 22, 24, 26, 28, 42, 44, and housing electrode 12 in order to monitor electrical activity of heart 16. Sensing module 102 may include a switch module to select which of the available electrodes are used to sense the cardiac electrical activity. The switch module may include a switch array, switch matrix, multiplexer, or any other type of switching device suitable to selectively couple electrodes to sensing module 102. In some examples, processor 106 selects the electrodes to function as sense electrodes, or the sensing vector, via the switch module within sensing module 102.

Sensing module 102 may include multiple sensing channels, each of which may be selectively coupled to respective combinations of electrodes 22, 24, 26, 28, 42, 44 and housing 12 to detect electrical activity of a particular chamber of heart 16, e.g. an atrial sensing channel and a ventricular sensing channel. Each sensing channel may comprise an amplifier that outputs an indication to processor 106 in response to sensing of a cardiac depolarization, in the respective chamber of heart 16. In this manner, processor 106 may receive sense event signals corresponding to the occurrence of R-waves and P-waves in the various chambers of heart 16. Sensing module 102 may further include digital signal processing circuitry for providing processor 106 with digitized EGM signals, which may be used for signal morphology analysis in some embodiments.

Memory 108 stores intervals, counters, or other data used by processor 106 to control the delivery of pacing pulses by therapy delivery module 104. Such data may include intervals and counters used by processor 106 to control the delivery of pacing pulses to heart 16. The intervals and/or counters are, in some examples, used by processor 106 to control the timing of delivery of pacing pulses relative to an intrinsic or paced event in another chamber. Memory 108 also stores intervals for controlling cardiac sensing functions such as blanking intervals and refractory sensing intervals. Events sensed by the sense amplifiers are identified based on their occurrence outside a blanking interval and inside or outside of a refractory sensing interval.

Event identification encoder 110 receives the sense signals corresponding to R-waves and P-waves from sensing module 102 or processor 106 and generates coded identification data of each sensed event. For example, sensing module 102 may output different logic level signals distinguishing between sensed events such as atrial sensed events, atrial refractory sensed events, ventricular sensed events and ventricular refractory sensed events. In response to the logic signals, event identification encoder 110 generates encoded data in a serial format to transmit to the telemetry module 112, for further transmission to programmer 30. The encoded data includes event markers in the form of logic level signals annotated with initials such as AS (atrial sense), ASR (atrial refractory sense), VS (ventricular sense) or VSR (ventricular refractory sense). Event identification encoder 110 may incorporate pacing events in the annotated logic level signals, including ventricular pacing pulse (VP) and atrial pacing pulse (AP) markers. Event markers are used by processor 106 in detecting and classifying cardiac rhythms and may be included in retrieved episode data used by programmer 30 to reclassify rhythm episodes.

In various embodiments, event identification encoder 110 may be implemented as digital logic circuitry or executable code stored in memory 108 executed by processor 106. Event identification encoder 110 may correspond generally to the marker channel logic disclosed in U.S. Pat. No. 4,374,382 (Markowitz), hereby incorporated herein by reference in its entirety. The encoded sensed event signals may be used by processor 106 in detecting and classifying a cardiac rhythm.

Programmer 30 includes a display 132, a processor 134, a user interface 136 and a communication module 138. A user, such as a physician, technician, nurse or other clinician, may interact with programmer 130 via user interface 136. For example, the user may interact with programmer 130 to retrieve currently programmed operating parameters, physiological data including EGM signal data collected by IMD 10, or device-related diagnostic information from IMD 10. A user may also interact with programmer 30 to program IMD 10, e.g., select values for operating parameters controlling the function of IMD 10. A user interacting with programmer 30 may interrogate IMD 10 to retrieve data accumulated and stored by IMD 10 and associated with detected and classified cardiac rhythm episodes. A user may view a display of a recorded EGM signal data with accompanying encoded event identification data to review and evaluate cardiac rhythm episodes. In some examples, episodes of recorded EGM signal data will be classified by IMD 10 as a particular cardiac rhythm such as sustained or non-sustained SVT, VT or VF. Data representative of classified cardiac rhythm episodes are transmitted from IMD 10 to programmer 30.

User interface 136 may include a graphical user interface and a mouse, pointer, keyboard, touch screen, or any combination thereof for enabling a user to interact with programmer 30. As will be further described below, a user may interact with programmer 30 via user interface 136 to provide expert "truthing" of cardiac rhythm episodes retrieved from IMD 10 and displayed on programmer 30. The user may approve recommended detection parameters identified by system 8 for programming into IMD 10 for real time detection and classification of cardiac rhythm episodes.

Programmer 30 includes a communication module 138 to enable wireless communication with IMD 10. Examples of communication techniques used by system 8 include low frequency or radiofrequency (RF) telemetry, which may be an RF link established via Bluetooth, WiFi, or MICS. Programmer 30 may include a programming head that is placed proximate to the patient's body near the IMD 10 implant site, and in other examples programmer 30 and IMD 10 may be configured to communicate using a distance telemetry algorithm and circuitry that do not require the use of a programming head and does not require user intervention to establish or maintain a communication link.

It is contemplated that programmer 30 may be coupled to a communications network via communications module 138 for transferring data to a remote database 150 or another computing device to allow remote monitoring and management of patient 14 using the techniques described herein. Reference is made to commonly-assigned U.S. Pat. Nos. 6,599,250 (Webb et al.), 6,442,433 (Linberg et al.), 6,418,346 (Nelson et al.), and 6,480,745 (Nelson et al.) for general descriptions and examples of network communication systems for use with implantable medical devices for remote patient monitoring and device programming, all of which patents are hereby incorporated herein by reference in their entirety. Remote patient management systems, such as the Carelink® Network (Medtronic, Inc., Minneapolis, Minn., USA) may be adapted to implement the presently disclosed techniques to accumulate cardiac rhythm episode data from a patient for use in performing detection simulations using various detection parameter settings to identify the recommended detection parameter settings for a given patient.

When programmer 30 is configured to perform a cardiac rhythm detection and classification simulation, communication module 148 may retrieve data from remote database 150 that has previously been retrieved from IMD 10 as well as retrieve new data from IMD 10 for use in a detection simulation performed by processor 134. In other embodiments, a processor associated with remote database 150 may accumulate patient episode data by retrieving the data from IMD 10 via programmer 30 during one or more interrogation sessions. The processor associated with remote database 150 may then perform the methods described herein for executing a detection simulation and identifying recommended detection parameter settings for a given patient.

The classification of cardiac episodes is initially performed in real-time by IMD 10 using signals received by sensing module 102 and cardiac events (P-waves and R-waves) identified by event identification encoder 110 according to one embodiment. Events are sensed by sensing module 102, which includes sense amplifiers with automatic adjusting sensing thresholds, for example as disclosed in U.S. Pat. No. 5,117,824 (Keimel et al.) and U.S. Pat. No. 6,249,701 (Rajasekhar, et al.), incorporated herein by reference in their entireties. An atrial sense amplifier and a ventricular sense amplifier receive EGM signals from selected electrodes 22, 24, 26, 28, 42, 44 and 12 and provide P-wave sense and R-wave sense output signals to event identification encoder 110 for use in generating the encoded event markers. As will be described herein, sensed events may be re-classified by reclassification module 140 included in programmer processor 134 and, in response to reclassifying sensed events within an episode, the cardiac rhythm classification may be reclassified for the episode. Sensed events are reclassified based on an analysis of the sensed event signals and/or digitized EGM signals for evidence of undersensing and oversensing. If sensed events are reclassified, e.g. if oversensed events are removed or undersensed events are added, the event intervals and event signal morphology may be recomputed and re-evaluated to determine a new classification of the episode.

Programmer 30 may be configured to display any reclassified cardiac rhythm episodes on display 132 and prompt a user to confirm the reclassification using the user interface 136. The user can review the displayed episode data and either confirm the reclassification, decline the reclassification to maintain the original classification, or, in some embodiments, manually select or enter a new classification. In this way, a clinician is relieved of the burden of reviewing every cardiac rhythm episode retrieved from the IMD for verification of proper sensing and episode detection, but expert input is requested to confirm or reject those episodes identified by the automatic reclassifications module as likely to be misclassified by the IMD. This expert "truthing" of the cardiac episode data provides a set of accurately classified rhythm episodes and greater confidence in the expected performance of recommended detection parameter settings identified after performing a detection simulation on the rhythm episodes as described further below.

In other embodiments, processor 134 may display original episodes and classifications and reclassified episodes on display 132. A user interacting with user interface 136 may be prompted to confirm or reject an episode classification or reclassification or input their own classification, allowing the expert user to make a final "truthed" classification of any or all recorded episodes.

A detection simulator 142 receives the retrieved episode data, which may include, but is not limited to, EGM records and corresponding event identification markers. Detection simulator 142 simulates detection of the retrieved episodes using the EGM signal data and detection parameters selected for optimization. Using at least two different settings for each detection parameter being evaluated, the detection simulator determines whether a rhythm classification made using the test parameter settings matches the truthed episode classifications. The detection simulator generates sensitivity and specificity data, e.g. in the form of receiver operating characteristic (ROC) curves, which are plots of the sensitivity versus specificity of the detection simulation results for each test parameter setting.

The "truthed" episode classifications are compared to episode classification results obtained by detection simulator 142 using the varied detection parameter settings to obtain percentages of specificity and percentages of sensitivity for each type of episode record, e.g. VF and VT, retrieved from the IMD 10.

Processor 134 may then generate a display of the sensitivity and specificity data, e.g. as ROC curves, on display 132, which may be in response to a user request. Processor 134 determines from the sensitivity and specificity data the detection parameter setting(s) which achieve a highest or targeted sensitivity and/or specificity for each type of rhythm detection, e.g. VF and VT. The recommended detection parameter setting(s) may be displayed on display 132 for approval by a user. Upon user confirmation, the detection parameter settings may be programmed into IMD 10 via communication module 138 and stored in memory 108 for use by processor 106 for real-time cardiac rhythm detection and classification.

The operations described herein for determining recommended detection parameter settings may be performed entirely by processor 134 executing instructions stored in a non-transitory computer-readable medium, e.g. associated memory 144. In other embodiments, a processor executing a detection simulation generating sensitivity and specificity data and identifying recommended detection parameters for a patient may be located remotely from patient 14 and programmer 30, in remote database 150. In this case, cardiac rhythm episode data acquired by IMD 10 is transmitted to remote database 150 via programmer 30 and a communication network, for example via the Internet or the Carelink® Network, during one or more interrogation sessions.

Figure 3:
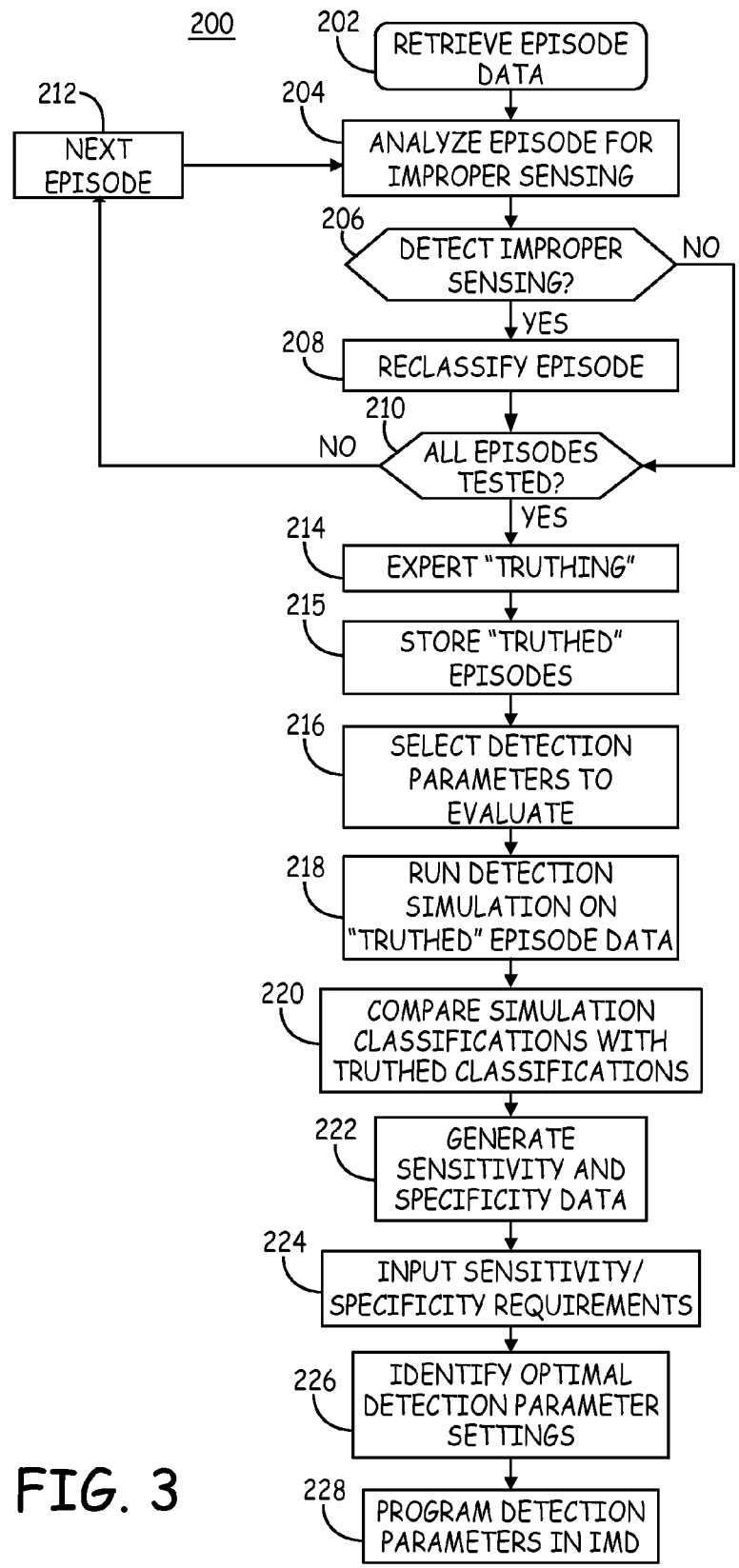
FIG. 3 is a flow chart of a method for identifying recommended cardiac rhythm episode detection parameter settings according to one embodiment.

FIG. 3 is a flow chart 200 of a method for identifying recommended cardiac rhythm episode detection parameter settings according to one embodiment. Flow chart 200 and other flow charts presented herein are intended to illustrate the functional operation of the medical device system, and should not be construed as reflective of a specific form of software or hardware necessary to practice the methods described. Methods described in conjunction with flow charts presented herein may be implemented in a non-transitory computer-readable medium that includes instructions for causing a programmable processor to carry out the methods described. A non-transitory computer-readable medium includes but is not limited to any volatile or non-volatile media, such as a RAM, ROM, CD-ROM, NVRAM, EEPROM, flash memory, or other computer-readable media, with the sole exception being a transitory, propagating signal. The instructions may be implemented as one or more software modules, which may be executed by themselves or in combination with other software.

At block 202, episode data is retrieved from IMD 10 by programmer 30. The episode data may include all stored episodes for a given patient, which may include any detected non-sustained or sustained episodes of VT, VF and SVT. The episode data can include an n-second recording of the EGM signal and encoded identification markers indicating sensed (and paced) events for each episode, e.g. Marker Channel data. In addition to or alternatively to retrieving episode data from the IMD, episode data previously transmitted from the IMD 10 to remote database 150, such as data previously transmitted to the Carelink® network, may be retrieved. The illustrative embodiment described in conjunction with flow chart 200 assumes that programmer 30 is retrieving all accumulated episode data from the IMD 10 and remote database 150 for a given patient to execute the methods of "truthing" the cardiac rhythm episodes, performing detection simulations using test parameter settings, and identifying the recommended detection parameter settings. As mentioned previously, however, these methods may be performed, all or in part, by IMD 10, programmer 30, or remote database 150.

The retrieved data may further include any templates used in classifying arrhythmias, such as a sinus R-wave template that may be used to discriminate between SVT and VT/VF. Normal EGM signal recordings, e.g. an n-second EGM transmission to Carelink® or other EGM signal recordings such as digital Holter recordings obtained by the IMD may also be retrieved. These EGM signal recordings may be used to generate a recommended morphology template for discriminating cardiac rhythm episodes during the detection simulation process.

Each cardiac rhythm episode is analyzed at block 204 to generate truthed cardiac rhythm episode data. In one embodiment, reclassification module 140 analyzes each retrieved episode to automatically verify the episode classification made by the IMD in real time. The reclassification module 140 automatically detects a misclassified episode of the retrieved cardiac rhythm episodes and determines a reclassification of the misclassified episode.

In one embodiment, each episode is analyzed for possible oversensing and undersensing. If oversensing or undersensing is detected, as determined at block 206, undersensed events may be added and oversensed events removed to enable recalculation of event intervals. The rhythm episode is then reclassified based on the recalculated, corrected event intervals. The methods used by reclassification module 140 for reclassifying episodes based on post-processing analysis for oversensing and undersensing may generally correspond to the methods disclosed in U.S. Pat. No. 8,073,536 (Gunderson, et al.) and U.S. Pat. No. 8,073,537 (Gunderson, et al.). The '536 and '537 patents are incorporated herein by reference in their entirety.

If no evidence of improper sensing, i.e., oversensing or undersensing, is detected in the current episode being evaluated at block 206, and additional episodes remain to be analyzed (decision block 210), the process advances to the next episode at block 212. After post-processing analysis of all retrieved episodes has been performed to automatically reclassify episodes as needed, the process advances to block 214.

In some embodiments, the programmer 30 requests expert confirmation of reclassified (and optionally originally classified) episodes. This expert "truthing" of episodes is optional in some embodiments in which the techniques described herein are fully automated but is required in other embodiments to ensure all retrieved episodes are accurately classified. A user may be prompted to confirm classification of all or a subset of episodes. For example, a user may be prompted to only confirm episodes that were originally classified as VT or VF and are reclassified as SVT automatically by reclassification module 140. In some embodiments, episode data corresponding to each episode that is automatically detected as a misclassified episode and reclassified by reclassification module 140 are displayed to a user and the user is prompted to confirm or reject the reclassified episode by confirming the reclassification or rejecting the reclassification. An expert user may reject the reclassification by confirming the original classification made by the IMD or by manually entering a "truthed" episode classification. The processor 134 receives an expert input via user interface 136 that confirms or rejects the reclassification of the cardiac rhythm episode, and stores a classification of the automatically detected misclassified episode in accordance with the expert input.

The automatic reclassification and expert truthing provides a set of episodes that are accurately classified. These "truthed" episodes are stored at block 215 and used to determine the sensitivity and specificity of a cardiac rhythm detection algorithm operating according to the same techniques used by the IMD but with varying detection parameter settings. After collecting a set of automatically reclassified and expert truthed cardiac rhythm episodes for the patient, the detection parameters to be evaluated are selected at block 216. The selection may be an automatic selection of default detection parameters or user-selected detection parameters. The detection parameters may include any or all parameters used by the IMD in controlling a detection algorithm.

Among the detection parameters that may be selected for evaluation are the detection interval (DI) for VF (FDI) and for VT (TDI), the number of detection intervals required to detect an episode (NID), and a morphology matching score threshold. The NID may be defined separately for the number of FDIs required to detect VF and the number of TDIs required to detect VT. Additionally a combined count of FDI and TDI may be used to detect a VT/VF episode. Parameters being evaluated may additionally or alternatively include enabling or disabling rules for discriminating SVT and VT such as a sinus tachycardia (ST) rule, atrial fibrillation (AF) rule, atrial flutter (AFL) rule, or an Other 1:1 SVT rule included a rule-based detection algorithm. Another parameter used to control a detection algorithm that may be evaluated is enabling or disabling the use of ATP for discriminating SVT from VT/VF. Any single parameter or combination of parameters used to control the detection algorithm may be evaluated.

When a parameter is selected for evaluation, each available setting for the parameter may be tested or a more limited number of selected values for the parameter may be tested. A clinician or other user may select which detection parameters and values are evaluated in a process for generating detection sensitivity and specificity data. The parameters used for cardiac rhythm detection and classification selected at block 216 will depend at least in part on the type of device performing automatic cardiac rhythm detection, the types of available sensors for sensing cardiac or hemodynamic signals used in detecting the cardiac rhythm, and the detection methods employed.

The TDI and FDI zones (overall therapy zone) define the ranges of RR intervals that are counted as a VT or VF interval by a detection counter. If a detection counter reaches a programmed NID, a detection is made. An SVT limit may be defined such that the SVT discrimination rules (e.g., AF, AFL, ST, Other 1:1 SVT rules) will only be applied to episodes with intervals longer than the SVT limit. Both individual VT and VF counters may be implemented as well as a combined VT/VF counter. In generating sensitivity and specificity data during the detection simulation, different cut-off intervals may be tested for separating the FDI and TDI zones and different SVT limits and/or different NIDs may be tested. Recommended FDI and TDI zones, SVT limits and/or NIDs may then be generated based on the sensitivity and specificity data.

Various rules used for discriminating between SVT and VT/VF are described in conjunction with rule-based detection algorithms disclosed, for example, in U.S. Pat. No. 5,545,186 (Olson et al.), U.S. Pat. No. 5,755,736 (Gillberg, et al.), U.S. Pat. No. 6,567,691 (Stadler), U.S. Pat. No. 7,031,771 (Brown, et al.), all of which patents are hereby incorporated by reference herein. Detection rules may include any of those listed above or in the cited references or variations thereof. A discrimination rule may be applied, for example, when the rate is within an SVT limit and a 1:1 correspondence between atrial and ventricular events is detected. When conditions for applying a rule are met, additional signal analysis may be performed, such as morphology template comparisons. The effect of enabling or disabling one or more rules on the detection sensitivity and specificity of the detection algorithm may be tested during a detection simulation as will be described below. In some embodiments, a threshold or other criterion defined for causing a rule to "fire" when the rule is enabled may be tested in addition to or alternatively to testing the detection algorithm with the rule enabled and disabled. An SVT rate limit may be varied while testing an SVT discrimination rule "ON" and "OFF".

Different templates used for morphology analysis may also be evaluated as different "settings" for the detection parameters. For example, multiple normal sinus rhythm templates may be tested to identify a template that provides the greatest sensitivity and specificity for detecting VT. Templates from different EGM sources (e.g. tip-ring electrodes, RVcoil-SVCcoil electrodes, RVcoil-housing electrode) may be tested to select the best EGM source. Normally conducted ventricular beats (i.e. R-waves) may be collected from a retrieved EGM signal recording to create sinus R-wave templates used for discriminating SVT and VT. R-waves used for generating a template may be selected from an EGM recording manually by a user or automatically based on interval patterns and/or consistent morphologies.

The use of ATP in discriminating SVT from VT/VF could be enabled or disabled in a detection algorithm. A response to ATP pulses, such as a measurement of a return cycle length is used in some embodiments discriminating between SVT and VT/VF. The use of ATP for rhythm discrimination and classification is generally disclosed in U.S. Pat. No. 7,149,577 (Sharma, et al.), U.S. Pat. No. 7,317,942 (Brown, et al.) and U.S. Patent Application Publication No. 2010/0198290 (Jackson, et al.).

The techniques described herein for identifying recommended detection parameters for a patient are not limited to implementation with a particular detection algorithm or detection parameters. Rather, any detection algorithm relying on one or more adjustable parameters may be used. The specific detection parameters and detection algorithms referred to herein are for illustration purposes and should not be construed as limiting the techniques to any particular algorithm, parameters, or parameter settings.

A detection simulation is executed at block 218. The detection algorithm executed by processor 30 uses the retrieved data and expert truthed episode classifications as input and applies the same detection algorithm as used by IMD 10 to the episode data with the exception of altering the settings of one or more detection parameters as selected at block 216. As such the detection algorithm simulates the IMD detection algorithm in order to identify detection parameter settings that meet or exceed specified sensitivity and specificity requirements.

The classification of each episode obtained by the detection algorithm for each test parameter setting is compared to the "truthed" episode classification at block 220. The specificity and sensitivity of each detection parameter setting can be determined and used to generate a specificity and sensitivity curve for the detection parameter The detection sensitivity for a given parameter setting (or combination of parameter settings) is the percentage of true VT and VF episodes detected by the detection simulation when operating according to the given control parameter setting(s). The detection specificity for the given parameter setting(s) is the percentage of true SVT episodes that are not detected as VT or VF. A multi-variate analysis may be performed in which all combinations of the parameter settings to be evaluated are applied and resulting sensitivity and specificity data generated.

At block 222, the sensitivity and specificity data is generated. In one embodiment, the sensitivity and specificity data are generated in the form of ROC curves, or other plots or curves that display the performance of the detection algorithm in correctly classifying the "truthed" episodes. An ROC curve plots the detection specificity vs. sensitivity for the range of detection parameter settings tested. Multiple curves may be plotted, one for each detection parameter tested. Additionally or alternatively, higher dimensional plots may be generated in which inter-dependencies of detection parameter settings are determined.

At block 224, the processor 134 receives sensitivity and specificity requirements which may be stored in associated memory (as default or programmed values) or input by a user via user interface 136. The specified sensitivity and specificity requirements may include a user defined best trade-off, e.g. a lower specificity may be acceptable when a higher sensitivity is desired. A user may have the option of selecting a minimum specificity required in order to achieve a selected sensitivity. In some embodiments, a minimum sensitivity and a minimum specificity may be established for each type of cardiac rhythm episode.

In one example embodiment, the programmer 30 or database 150 may be configured to provide a display of a maximum specificity reached for the tested parameter settings for multiple sensitivity settings. For example, a user may input a 100% sensitivity requirement and be presented with the maximum specificity possible. The user may then decrease the sensitivity requirement to view the effect on the maximum specificity reached for a lower sensitivity. Alternatively a table or graph of the sensitivity and specificity data maybe generated and displayed so that a user may select or view a detection sensitivity and observe a resulting specificity from the displayed data. In this way, the user is able to make an informed decision in specifying a required sensitivity that may result in a trade-off of lower specificity.

A detection interval safety margin may additionally be provided as input at block 224. It is desirable for a detection interval (DI), e.g. FDI, to be programmed to be a safety margin longer than a longest detection interval that would be required to detect all true episodes, e.g. true VF episodes, retrieved for a given patient. The DI safety margin may be provided as input at block 224 by a user or be a stored default value. The DI safety margin provides greater certainty in detecting future episodes because episode cycle lengths may vary due to medication changes or other factors. The safety margin provides a margin of confidence in detecting all true episodes even when variations in cycle length may occur. A default safety margin value may be 30 ms, for example.

The recommended setting for each detection parameter evaluated is identified at block 226 such that an overall combination of recommended settings meets the specified sensitivity and specificity requirements, and a safety margin when specified. If more than one combination of settings meets a required sensitivity, the combination of detection parameter settings resulting in the highest specificity is selected.

In some cases, if more than one set of detection parameter settings meet the sensitivity and specificity requirements, parameter settings that minimize processing time or burden or provide greatest safety margin for detecting VF are selected. For example, some detection rules may be disabled if minimum acceptable sensitivity and specificity requirements are met to reduce IMD processing burden. It is recognized that in some embodiments the minimum acceptable specificity requirement may be 0% (i.e. no specificity requirement). If no specificity requirement is specified, the sensitivity may be maximized to promote 100% detection of all VT and VF episodes.

The recommended settings are programmed into the IMD 10 at block 228 for use as the detection parameter settings during real-time detection and classification of cardiac rhythm episodes by IMD 10. Programming may be automatic or performed after user approval of any changed parameter settings.

Figure 4:
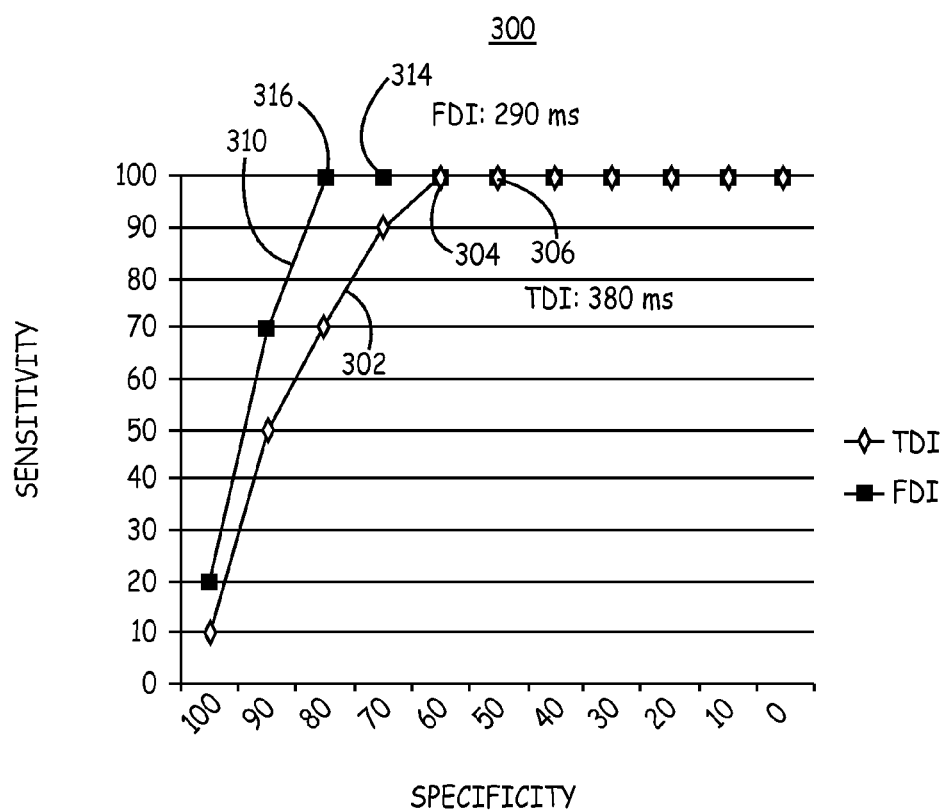
FIG. 4 is a sample receiver operating characteristic (ROC) plot generated using the techniques described in conjunction with FIG. 3.

FIG. 4 is a sample ROC plot 300 generated using the techniques described in conjunction with FIG. 3. For the sake of simplification, sensitivity and specificity data is shown in two-dimensional ROC curves for a given detection parameter. It is recognized, however, that the detection simulation may generate a multivariate analysis that identifies the percentage sensitivity and specificity for all combinations of multiple detection parameters being evaluated and this data may be stored and presented in a tabular or graphical format.

In plot 300, an ROC curve 302 is shown for varying TDI settings, and an ROC curve 310 is shown for varying FDI settings. Sensitivity is plotted along the y-axis from 0 to 100%, and specificity is plotted along the x-axis from 100% to 0. When the TDI is increased from 300 ms to 500 ms, the ROC curve 302 shows that specificity decreases from 100% to 0% and sensitivity increases from 10% to 100%. In other words, at the longest setting of 500 ms, all VT episodes are detected (high sensitivity) but SVT episodes are also detected as VT (low specificity). A TDI of 380 ms 306 resulting in 100% sensitivity for detecting all true VT episodes results in approximately 50% specificity. This TDI setting 306 may be selected as the TDI when a targeted sensitivity is at or near 100%. The TDI setting 306 provides for a required DI safety margin that is greater than the safety margin provided by the preceding TDI setting represented by point 304.

When the FDI is increased from 240 ms to 360 ms, the ROC curve 310 shows that specificity decreases from 100% to 0% and sensitivity increases from 20% to 100%. An FDI of 290 ms 314 results in 100% sensitivity with approximately 70% specificity. In order to meet a safety margin requirement, the FDI of 280 ms 314 may be selected to include, for example, a 30 ms safety margin such that all retrieved and truthed VF episodes would be detected while allowing a safety margin for fluctuation of the VF interval in future episodes. The FDI at point 316 on the ROC curve reaches 100% sensitivity but may not include a required safety margin to allow for fluctuations in fibrillation intervals.

Figure 5:
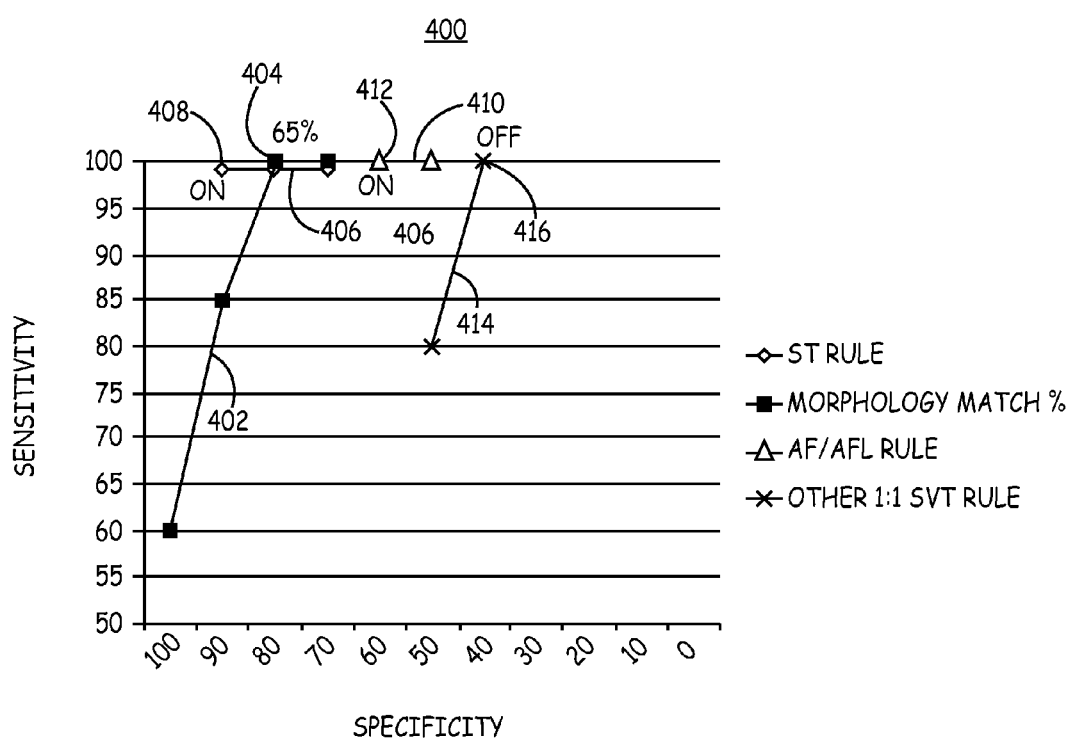
FIG. 5 is a plot of sensitivity and specificity data for multiple detection parameter settings tested during a detection simulation.

FIG. 5 is an ROC plot 400 for multiple detection parameter settings tested during a detection simulation executed on a set of truthed episodes. In this illustrative example, the detection parameters being evaluated include a morphology matching threshold, an ST rule, an AF/AFL rule and an Other 1:1 SVT rule. The morphology matching threshold is used to discriminate between SVT and VT by determining if an R-wave signal morphology approximately matches a normal sinus rhythm (NSR) morphology indicating the R-wave has been conducted from the atria and the rhythm is a supraventricular rhythm. The morphology matching score may be evaluated during the detection simulation at settings starting at 70% and decreasing to 55% in one example, though higher and lower matching score thresholds may be tested.

The other parameters, e.g., the ST rule, AF/AFL rule and other 1:1 rule, may be tested as being enabled (ON) or disabled (OFF). Plot 400 shows the resulting sensitivity and specificity of each parameter setting.

The morphology matching threshold ROC curve 402 shows 100% sensitivity with a matching threshold of 65% at point 404. Lower morphology matching thresholds result in lower sensitivity. Separate ROC curves could be displayed for different templates obtained from the same or different EGM source electrodes (e.g. tip-ring, RVcoil-SVCcoil) to generate sensitivity and specificity data for each template used for morphology comparisons.

The ROC curves 406, 410 and 414 corresponding to the tested ST rule, AF/AFL rule, and other 1:1 SVT rule respectively. Curve 406 presents approximately the same sensitivity for both ON and OFF settings of the ST rule. The ON setting resulting in point 408, however, results in higher specificity. Accordingly, the recommended setting for the ST rule would be ON for obtaining higher specificity, but may be recommended to be OFF in some embodiments to reduce processing time if a targeted specificity is already reached with the ST rule OFF.

Similarly the AF/AFL Rule ROC curve 410 shows a result of 100% sensitivity for both ON and OFF settings but provides higher specificity when programmed ON as shown by point 412. The ROC curve 414 for the Other 1:1 SVT rule tested ON and OFF results in 80% sensitivity when ON and 100% sensitivity when OFF at point 416. The OFF setting is recommended toward for promoting 100% sensitivity in detecting all true VT and VF rhythms. Based on the ROC curves shown in plot 400, the recommended IMD programming for the parameters tested would include 65% morphology match threshold, ST rule ON, AF/AFL rule ON, and Other 1:1 SVT rule OFF for real-time cardiac rhythm detection. The recommended settings may be displayed on display 132 or on a remote computer in communication with remote database 150 and automatically programmed via telemetry.

In some embodiments, clinician approval is required before automatic programming of the recommended settings is performed.

Figure 6:
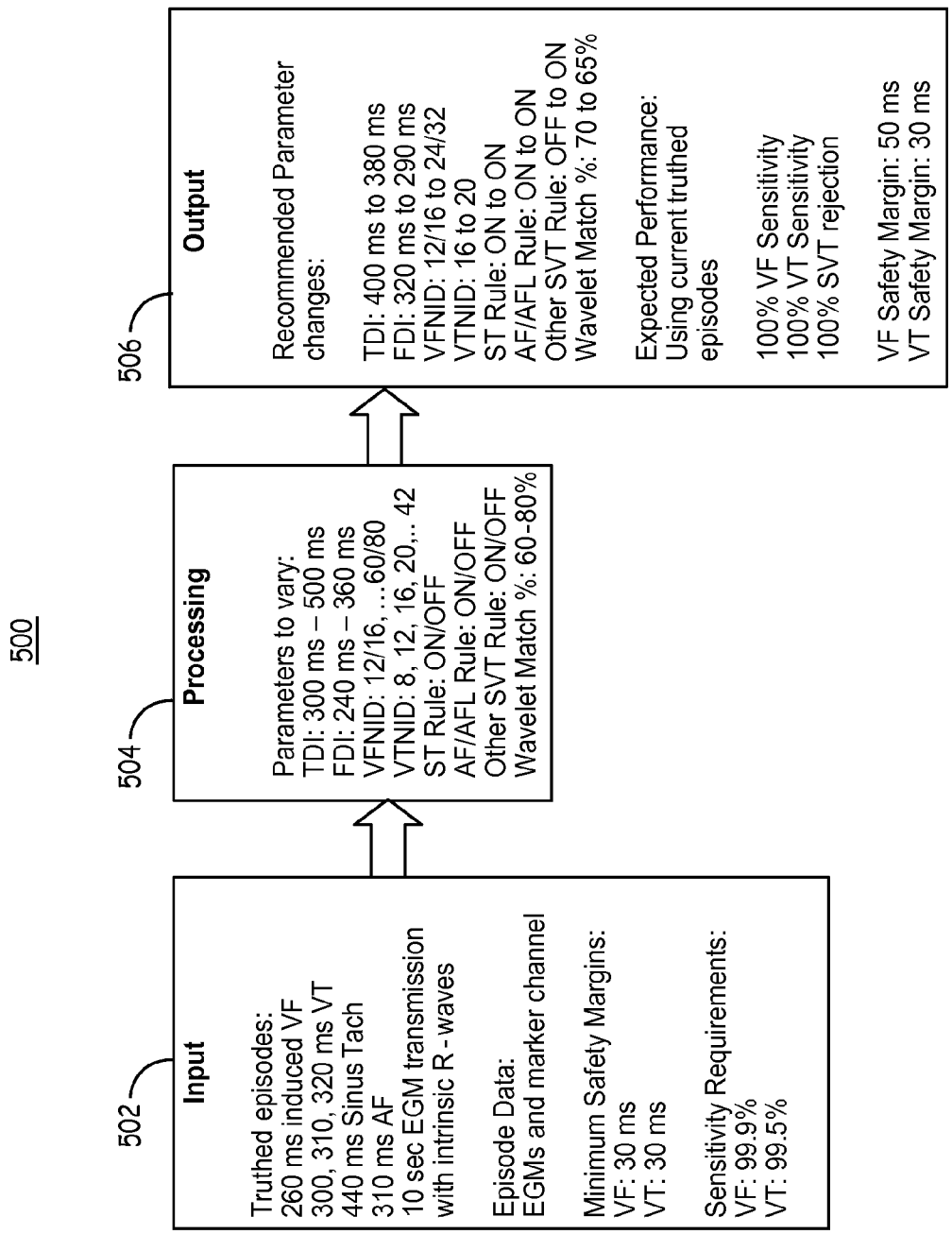
FIG. 6 is a data flow diagram illustrating a determination of recommended detection parameter settings for a sample data set according to the techniques described herein.

FIG. 6 is a data flow diagram 500 illustrating a determination of recommended detection parameter settings for retrieved episode data according to the techniques described herein. Input block 502 provides a summary of at least a portion of the data that is provided to processing block 504. Input block 502 includes a set of truthed cardiac rhythm episodes that have been analyzed by an automatic reclassification module and at least a portion of episodes reclassified by automatic reclassification module confirmed by an expert user.

In this example data set, the truthed episodes include an induced VF episode having an average cycle length of 260 ms, three VT episodes having average cycle lengths of 300, 310 and 320, a sinus tachycardia episode having a cycle length of 440 ms, and an episode of AF having an average cycle length of 310 ms. The truthed episode data includes EGM signal data recorded for each episode, e.g. a 10-second EGM recording, and encoded identification marker channel data.

Other input may include a required minimum safety margin, minimum sensitivity and minimum specificity. These requirements may be default requirements or input by a user. The sensitivity requirement provides a minimum acceptable detection sensitivity that must be met by the recommended detection parameter settings identified by processing block 504. The sensitivity may be set differently for detecting VF than for detecting VT. It may be desirable to achieve a high sensitivity, e.g. greater than 99%, for VT and VF since these rhythms can be serious and life threatening. A lower specificity may be acceptable in order to achieve high sensitivity. In other words, a higher number of false positive detections may be accepted in order to achieve 100% or nearly 100% detection (or other specified sensitivity) of all true VT and VF episodes. A DI safety margin that increases the TDI or the FDI may result in a lower specificity but may be recommended in order to meet or exceed a specified sensitivity and take into account possible fluctuations in tachycardia or fibrillation intervals.

Processing block 504 performs a detection simulation using the truthed episode data while varying selected detection parameter settings. In the example shown, the maximum TDI is varied from 300 ms to 500 ms, the maximum FDI is varied from 240 ms to 360 ms, VF NID may be varied from 12/16 up to 60/80 (number of VF intervals out of a consecutive number of R-R intervals), and VT NID may be varied between 8 and 42. The ST rule, AF/AFL rule, and other 1:1 SVT rule are tested ON and OFF. The morphology wavelet matching threshold score is varied between 60% and 80%. These test settings are illustrative in nature and it is recognized that the number of parameters tested and the number and range of settings tested for each parameter may vary between embodiments and may be tailored by a user or automatically based on previous simulation results for a particular patient.

After running the detection simulation on each episode for every combination of detection parameter settings, sensitivity and specificity data are generated. By implementing the detection simulation algorithm in an external device having greater processing power than that available in the implantable device, it is feasible to perform a multi-variate analysis to determine the sensitivity and specificity for every combination of test settings. Alternatively, each parameter may be tested individually while other test settings are held fixed at default or most recently programmed values.

A setting for each parameter that meets the input sensitivity requirement is selected. If more than one setting for a given parameter meets the input sensitivity requirement, additional criteria may be applied. For example, the setting that meets the sensitivity requirement with a highest specificity may be recommended. In another example, a setting that is enabled or disabled may be disabled if the sensitivity requirement is still met and processing burden can be reduced. In another example, a setting that will result in a faster detection, for example a relatively lower NID as compared to a higher NID, may be selected. A detection interval may be selected as the longest detection interval that provides the required sensitivity and still meets a minimum specificity when specified.

Output block 506 lists the recommended detection parameter settings. Changes from a currently programmed setting to an identified optimal setting for each of the tested parameters are shown. The expected performance of the detection algorithm using the recommended parameter settings is also listed based on the results of the detection simulation applied to the truthed episodes. The expected performance is presented as an expected VF sensitivity (rate of detecting true VF), an expected VT sensitivity (rate of detecting true VT) and an expected specificity (rate of rejecting SVT, i.e. not detecting as VT or VF), are displayed.

Additionally, a VF safety margin and VT safety margin are listed. The VF or VT safety margin is computed as the difference between the recommended FDI or TDI, respectively, and a longest interval measurement characterizing truthed VF and/or VT episodes. For example, if the recommended FDI is 290 ms and the slowest true VF episode is characterized by a VF interval of 240 ms, the VF safety margin is 50 ms. In another example, a VT safety margin of 30 ms is computed as the difference between a recommended VTI of 380 ms and the slowest true VT episode characterized by an RR interval measurement of 350 ms. The longest VF or VT interval characterizing a slowest truthed episode may be determined in a number of ways. It may be the longest VF or VT interval measured for all truthed episodes or the greatest value of a specified percentile of all intervals contributing to a truthed episode.

In some embodiments, the recommended parameter changes are automatically programmed in the IMD 10. In other embodiments, the data listed in the output block 506 may be displayed to a user for approval prior to any reprogramming. In some examples, a clinician may be able to alter one or more of the recommended settings to a different setting and a displayed expected sensitivity and specificity will be automatically adjusted according to the generated sensitivity and specificity data.

The blocks 502, 504 and 506 represent both functional operations performed and actual displays that may be presented to a user. In other words, the information shown in blocks 502, 504 and 506 or some variation thereof may be presented on display 132 as shown in FIG. 6. The user is then informed about what data is used as input to the detection simulation (block 502), what parameters are varied and what settings are used during the detection simulation (block 504) and the resulting recommended settings and expected performance (block 506).

Each block 502, 504 and 506 may be interactive allowing a user to adjust input safety margin and sensitivity or specificity (not shown) requirements (block 502), adjust parameters and/or settings to be evaluated (block 504), and/or adjust the recommended parameter changes or the expected performance (sensitivity, specificity and/or safety margin (block 506). In this way, the user can observe the effects of changing an input, a tested setting, and/or a recommended parameter change on the expected performance. Conversely, the user can observe the effects of changing expected performance on the recommended parameter changes by interacting with a display of blocks 502, 504 and 506.

Figure 7:
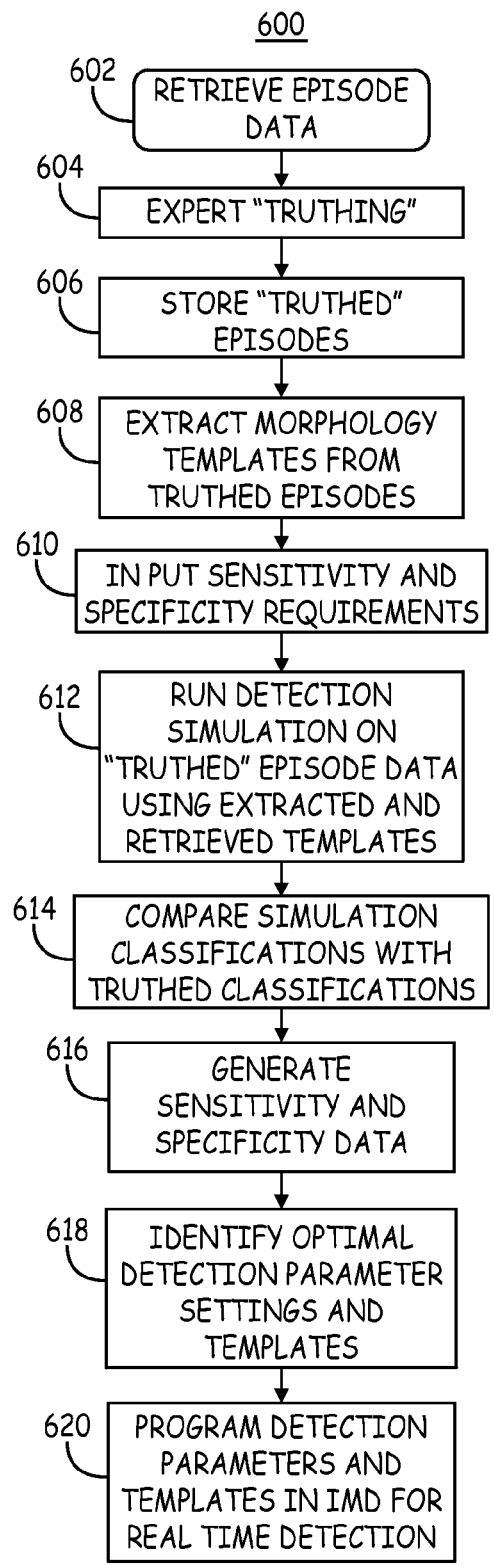
FIG. 7 is a flow chart of techniques used for identifying recommended detection parameter settings according to one embodiment.

FIG. 7 is a flow chart 600 of techniques used for identifying recommended detection parameter settings according to one embodiment. At block 602, episode data is retrieved as described previously. At block 604, expert truthing provides expert-verified classification of the retrieved episode data such that "truthed" episodes can be stored at block 606, which may include true VT and VF episode detections, false VT or VF episode detections reclassified as SVT, and false SVT detections reclassified as VT or VF. As described previously, automatic reclassification of retrieved episode data may be performed with expert verification of any reclassified episodes.

At block 608, morphology templates are extracted from the truthed episodes. A morphology template may be extracted from one or more truthed episodes automatically or manually. For example, the processor may automatically select a single QRS signal complex from a truthed episode. An R-wave template may be computed from the QRS complex, such as a wavelet template. That R-wave template may then be stored as a template for detecting the type of rhythm corresponding to the truthed episode, which may be an SVT or VT episode. Since a patient may present more than one type of VT and more than one type of SVT rhythm, multiple templates may be stored for multiple SVT episode types and/or multiple VT episode types.

The sensitivity and specificity requirements are provided prospectively as input to the detection parameter selection algorithm at block 610 or may be established after sensitivity and specificity data is generated as described previously. At block 612, the detection simulation is run on the truthed episode data. Whenever a morphology analysis is performed as part of the detection algorithm, the templates extracted from the truthed episodes and/or any normal sinus rhythm template(s) retrieved from the IMD or extracted from an EGM recording may be used.

The episode classifications arrived at during the simulation are compared to the truthed episode classifications at block 614. Sensitivity and specificity data is generated at block 616, which may be displayed as ROC curves in some embodiments. The detection simulation may determine the detection sensitivity and specificity of the detection algorithm when different templates are used when morphology comparisons are made. In this way, the use of templates for morphology comparisons can be optimized such that one or more VT and/or one or more SVT templates can be identified, along with other recommended detection parameters, which result in a specified sensitivity and specificity, at block 618.

The recommended detection parameters including recommended morphology templates identified at block 618 are programmed into the IMD at block 620, either automatically or upon user authorization, for use during real time rhythm detection and classification. In this way, expert truthed morphology templates that meet or exceed a targeted sensitivity and specificity can be identified and can include both VT templates and SVT templates to improve the confidence in real-time detection and discrimination of cardiac rhythm episodes. The addition of using a VT template extracted from an expert truthed VT episode may represent an addition to the detection algorithm utilized by the IMD.

Thus, a system and method for selecting cardiac rhythm detection parameters have been presented in the foregoing description with reference to specific embodiments. It is appreciated that various modifications to the referenced embodiments may be made without departing from the scope of the disclosure as set forth in the following claims.

The invention claimed is:

1. A method for determining detection parameters in a medical device, comprising:
   enabling a communication module to retrieve stored episode data accumulated by a medical device configured to sense cardiac signals and detect cardiac rhythm episodes from the sensed cardiac signals in real time using a detection algorithm controlled by a plurality of detection parameters;
   generating truthed episode classifications from the retrieved episode data by enabling a reclassification module to automatically detect a misclassified episode of the detected cardiac rhythm episodes, determine a reclassification of the misclassified episode, display retrieved episode data corresponding to the misclassified episode, receive an expert input that confirms or rejects the reclassification of the misclassified episode, and store a classification of the automatically detected misclassified episode in accordance with the expert input;
   enabling a processor to perform a detection simulation for detecting and classifying each of the cardiac rhythm episodes included in the retrieved episode data using the detection algorithm and varied settings of the plurality of detection parameters to obtain simulated episode classifications;
   generating detection sensitivity and specificity data in response to the detection simulation by comparing the truthed episode classifications to the simulated episode classifications;
   receiving, by the processor, a detection sensitivity requirement for detecting a tachyarrhythmia and a detection specificity requirement for detecting the tachyarrhythmia; and
   in response to the sensitivity and specificity data, enabling the processor to identify a recommended detection parameter setting that causes the simulated episode classifications to meet the detection sensitivity requirement and the detection specificity requirement.

2. The method of claim 1, further comprising automatically programming the recommended detection parameter setting in the medical device sensing the cardiac signals for use in detecting cardiac rhythm episodes in real time.

3. The method of claim 1, further comprising displaying a subset of the automatically detected misclassified episodes for receiving the expert input to confirm or reject a reclassification of each misclassified episode of the subset.

4. The method of claim 1, further comprising:
   establishing the detection sensitivity requirement in response to a user input sensitivity; and
   enabling the processor to identify a set of recommended settings of the detection parameters that causes the simulated episode classifications to meet the sensitivity requirement.

5. The method of claim 4, further comprising:
   establishing the detection specificity requirement in response to a user input specificity; and
   enabling the processor to identify the set of recommended settings of the detection parameters to additionally meet the specificity requirement.

6. The method of claim 5, further comprising displaying the generated sensitivity and specificity data, wherein establishing at least one of the specificity and the sensitivity requirement comprises receiving a user input in response to the displayed sensitivity and specificity data.

7. The method of claim 1, further comprising displaying to a user a maximum specificity resulting from the detection simulation for a given detection sensitivity.

8. The method of claim 1, further comprising displaying an expected sensitivity and specificity corresponding to the recommended detection parameter setting;
   altering the recommended detection parameter setting in response to a user input; and
   displaying an adjusted sensitivity and specificity for the altered recommended detection parameter setting.

9. The method of claim 1, wherein the plurality of detection parameters comprise a morphology template and further comprising:
   enabling the processor to extract a ventricular tachycardia template from a truthed episode, apply the ventricular tachycardia template during the detection simulation for classifying the retrieved episode data, and identifying a recommended a ventricular tachycardia template extracted from a truthed episode in response to the sensitivity and specificity data; and
   programming the recommended ventricular tachycardia template in the medical device for use in detecting cardiac rhythm episodes in real time.

10. The method of claim 9, further comprising selecting a truthed cardiac episode having a classification stored in response to the expert input; and
   extracting the ventricular tachycardia template from the selected truthed cardiac episode.

11. The method of claim 1, further comprising retrieving an EGM recording recorded by the medical device, computing a morphology template from the EGM recording, enabling the processor to execute the detection simulation using a plurality of different morphology templates, and identifying a recommended morphology template as one of the detection parameter settings.

12. The method of claim 1, further comprising:
   storing a required detection interval safety margin; and
   identifying the recommended detection parameter setting in response to the sensitivity and specificity data and the required safety margin.

13. A system, comprising:
   a medical device configured to sense cardiac signals and detect cardiac rhythm episodes from the sensed cardiac signals in real time using a detection algorithm controlled by a plurality of detection parameters;
   a communication module to retrieve stored episode data accumulated by the medical device;
   a display for displaying data to a user;
   a user interface for receiving input from a user interacting with the system;
   a reclassification module coupled to the display, the user interface and the communication module and configured to receive the episode data and generate truthed episode classifications by automatically detecting a misclassified episode of the detected cardiac rhythm episodes, determining a reclassification of the misclassified episode, displaying retrieved episode data on the display corresponding to the misclassified episode, receiving an expert input via the user interface that confirms or rejects the reclassification of the misclassified episode, and storing a classification of the automatically detected misclassified episode in accordance with the expert input; and
   a processor configured to:
   perform a detection simulation for detecting and classifying each of the cardiac rhythm episodes included in the retrieved episode data using the detection algorithm and varied settings of the plurality of detection parameters to obtain simulated episode classifications, generate detection sensitivity and specificity data in response to the detection simulation by comparing the truthed episode classifications to the simulated episode classifications, receive a detection sensitivity requirement for detecting a tachyarrhythmia and a detection specificity requirement for detecting the tachyarrhythmia, and in response to the sensitivity and specificity data, identify a recommended detection parameter setting that causes the simulated episode classifications to meet the detection sensitivity requirement and the detection specificity requirement.

14. The system of claim 13, wherein the processor and communication module are configured to automatically program the recommended detection parameter setting in the medical device sensing the cardiac signals for use in detecting cardiac rhythm episodes in real time.

15. The system of claim 13, wherein the reclassification module, the display and the user interface are further configured to display a subset of automatically detected misclassified episodes and receive the expert input to confirm or reject a reclassification of each misclassified episode of the subset.

16. The system of claim 13, further comprising:
a memory storing the detection sensitivity requirement, the detection sensitivity requirement input by a user
the processor configured to identify a set of recommended settings of the detection parameters that causes the simulated episode classifications to meet the sensitivity requirement.

17. The system of claim 16, further comprising:
a memory storing a specificity requirement, the detection specificity requirement input by a user,
the processor configured to identify the set of recommended settings of the detection parameters to additionally meet the specificity requirement.

18. The system of claim 17, wherein the processor and the display are configured to display the generated sensitivity and specificity data,
the memory configured to store at least one of the sensitivity requirement and the specificity requirement in response to a user input received via the user interface in response to the displayed sensitivity and specificity data.

19. The system of claim 13, wherein the processor and display are further configured to display a maximum specificity resulting from the detection simulation for a given detection sensitivity.

20. The system of claim 13, wherein the processor and display are further configured to display an expected sensitivity and specificity corresponding to the recommended detection parameter setting;
the processor configured to alter the recommended detection parameter setting in response to receiving a user input via the user interface; and
the processor generating an adjusted sensitivity and specificity for the altered recommended detection parameter setting and displaying the adjusted sensitivity and specificity on the display.

21. The system of claim 13, wherein the detection parameters comprise a morphology template and further comprising:
the processor configured to extract a ventricular tachycardia template from a truthed episode, apply the ventricular tachycardia template during the detection simulation for classifying the retrieved episode data, and identify a recommended ventricular tachycardia template extracted from a truthed episode in response to the sensitivity and specificity data,
the processor and communication module configured to program the recommended ventricular tachycardia template in the medical device for use in detecting cardiac rhythm episodes in real time.

22. The system of claim 21, wherein the processor is further configured to select a truthed cardiac episode having a classification stored in response to the expert input, and
extract the ventricular tachycardia template from the selected truthed cardiac episode.

23. The system of claim 13, wherein the processor is further configured to retrieve an EGM recording recorded by the medical device, compute a morphology template from the EGM recording, execute the detection simulation using a plurality of different morphology templates, and identify a recommended morphology template as one of the detection parameters settings.

24. The system of claim 13, further comprising:
a memory storing a required detection interval safety margin; and
the processor further configured to identify the recommended detection parameter setting in response to the sensitivity and specificity data and the required safety margin.

25. A non-transitory computer-readable medium comprising instructions for causing a processor of a medical device system to perform a method, the method comprising:
retrieving stored episode data accumulated by a medical device configured to sense cardiac signals and detect cardiac rhythm episodes from the sensed cardiac signals in real time using a detection algorithm controlled by a plurality of detection parameters;
generating truthed episode classifications from the retrieved episode data by detecting a misclassified episode of the detected cardiac rhythm episodes, determining a reclassification of the misclassified episode, displaying retrieved episode data corresponding to the misclassified episode, receiving an expert input that confirms or rejects the reclassification of the misclassified episode, and storing a classification of the automatically detected misclassified episode in accordance with the expert input;
performing a detection simulation for detecting and classifying each of the cardiac rhythm episodes included in the retrieved episode data using the detection algorithm and varied settings of the plurality of detection parameters to obtain simulated episode classifications;
generating detection sensitivity and specificity data in response to the detection simulation by comparing the truthed episode classifications to the simulated episode classifications;
receiving a detection sensitivity requirement for detecting a tachyarrhythmia and a detection specificity requirement for detecting the tachyarrhythmia; and
in response to the sensitivity and specificity data, identifying a recommended detection parameter setting that causes the simulated episode classifications to meet the detection sensitivity requirement and the detection specificity requirement.

* * * * *